United States Patent [19]

Risebury

[11] 4,322,558
[45] Mar. 30, 1982

[54] OXIDATION PROCESS

[75] Inventor: John F. Risebury, Middlesbrough, England

[73] Assignee: Imperial Chemical Industries Limited, London, England

[21] Appl. No.: 857,971

[22] Filed: Dec. 5, 1977

[30] Foreign Application Priority Data

Dec. 31, 1976 [GB] United Kingdom ............... 54424/76

[51] Int. Cl.$^3$ ....................... C07C 45/33; C07C 29/52
[52] U.S. Cl. ..................................... 568/359; 568/837
[58] Field of Search ................. 260/586 AB; 568/837, 568/359

[56] References Cited

U.S. PATENT DOCUMENTS

| | | | |
|---|---|---|---|
| 3,336,390 | 8/1967 | Nelsen et al. ................ | 260/586 AB |
| 3,419,615 | 12/1968 | Inchalik et al. .............. | 260/586 AB |
| 3,927,105 | 12/1975 | Brunie et al. ................ | 260/586 AB |
| 3,932,513 | 1/1976 | Russell ......................... | 260/586 AB |
| 3,987,100 | 10/1976 | Barnette et al. ............. | 260/586 AB |
| 4,042,630 | 8/1977 | Wolters et al. .............. | 260/586 AB |
| 4,058,565 | 11/1977 | Theil et al. .................. | 568/359 |

FOREIGN PATENT DOCUMENTS

| | | | |
|---|---|---|---|
| 38774 | 6/1960 | Japan ........................... | 260/586 AB |
| 4720618 | 10/1968 | Japan ........................... | 260/586 AB |

*Primary Examiner*—Nicky Chan
*Assistant Examiner*—James H. Reamer
*Attorney, Agent, or Firm*—Cushman, Darby & Cushman

[57] ABSTRACT

The oxidation product of cyclohexane with an oxygen-containing gas in presence of a boron compound is, after hydrolysis and separation of boric acid, deperoxidized with a heavy metal catalyst, especially a chromium salt.

10 Claims, No Drawings

OXIDATION PROCESS

This invention relates to the oxidation of cycloalkanes to cycloalkanols and cycloalkanones.

According to the invention a process for the manufacture of cyclohexanol and cyclohexanone comprises oxidising cyclohexane in the liquid phase with a molecular oxygen-containing gas in the presence of a boron compound with partial conversion of cyclohexane to give an oxidate comprising cyclohexane, boric esters of cyclohexanol and cyclohexylhydroperoxide, treating the said oxidate with water to hydrolyse the said boric esters to cyclohexanol and boric acids, separating the water and boric acids and treating the organic residue with a cyclohexane-soluble peroxide- decomposing heavy metal compound to decompose the cyclohexyl-hydroperoxide, and separating cyclohexane from the resulting cyclohexanol and cyclohexanone.

The oxidation of cyclohexane in the liquid phase with a molecular oxygen-containing gas in the presence of a boron compound to give cyclohexanol and cyclohexanone is already known and is described, for example, in British Patent Specifications Nos. 996,791 and 996,792 and the oxidation stage of our process follows this prior art teaching. The molecular oxygen-containing gas may be oxygen itself but is preferably a mixture of oxygen with an inert gas, for example nitrogen. Air is a particularly convenient gas mixture to use, although mixtures of air with oxygen or nitrogen and therefore having a higher or lower oxygen content than air itself may also be used.

The boron compound is preferably metaboric acid or dehydrated forms of orthoboric acid, but may be boron oxide, tetraboric acid or borate esters such as cyclohexyl metaborate, or methyl or ethyl borate. The boron compound is generally employed in amounts of at least 1 mole of boron compound (expressed as metaboric acid) per 6 moles of cyclohexane oxidised. The degree of conversion of the cyclohexane is generally from 4% to 25%.

The oxidation temperature is generally from 140° to 180° C., preferably from 160° to 170° C., the pressure being at least sufficient to keep the cyclohexane substantially in the liquid phase, pressures up to about 50 bar being contemplated. Water is formed during the oxidation reaction, and it is desirable to remove water as it is formed to prevent the formation of higher hydrates of boric acid, by distilling off water, possibly together with some cyclohexane, as the oxidation proceeds. British Patent Specification No. 996,791 prescribes a maximum partial pressure of water over the reaction mixture for optimum results.

At this stage the oxidate (other than unconverted cyclohexane) consists primarily of cyclohexyl borates. It also contains small amounts of cyclohexanone (up to about 10% of the cyclohexane converted) and of cyclohexyl hydroperoxide (up to 20% or more of the cyclohexane converted), and small amounts of by-products. It is then convenient to remove a part of the cyclohexane, conveniently in a flash column and at the same time reducing the pressure near to that of the atmosphere. The oxidate is then treated with water to hydrolyse the cyclohexyl borates to cyclohexanol and boric acid, again according to prior art teaching. Treatment takes place at temperatures above about 50° C., and results in an organic portion containing cyclohexane, cyclohexanol, cyclohexanone and cyclohexylhydroperoxide, and an aqueous portion consisting of a solution or suspension of boric acid, and also containing water-soluble by-products. The boric acid, after suitable treatment may be recycled to the oxidation. Such treatment may include a purge to reduce the level of impurities, and dehydration to bring the boric acid to the level of hydration desired for the oxidation process.

According to our invention the organic residue is then treated with a cyclohexane-soluble peroxide-decomposing heavy metal compound to decompose the cyclohexyl-hydroperoxide. Preferred heavy metal compounds are cobalt compounds and more especially chromium compounds. The heavy metal compounds should be soluble in cyclohexane, and particularly preferred are salts of aliphatic or cycloaliphatic carboxylic acids, especially those having from 5 to 12 carbon atoms, or of mixtures thereof. Examples of particularly suitable salts of this kind are cobalt or chromium naphthenate or octoate. The heavy metal compound is preferably added to the organic residue as a solution in a hydrocarbon, for example in white spirit, but more especially in cyclohexane itself. The amount of heavy metal compound it is convenient to use may vary, for example, from 0.5 to 50 parts per million (p.p.m.) by weight preferably 1 to 10 p.p.m., calculated as metal and expressed on the total weight of the organic residue, though larger amounts may, of course, be used, and smaller amounts may be effective if the treatment is prolonged. The treatment is effected by heating at temperatures, for example in the range 70° to 200° C., preferably 90° to 130° C., for periods which may vary, for example, from a few minutes, e.g. 5 minutes, to several hours, e.g. 5 hours.

The treatment may be carried out as a separate step or may conveniently be combined with the removal of at least some of the remaining cyclohexane by distillation. Thus, for example, a solution of the heavy metal compound may be introduced into the organic residue immediately before it is introduced into a still for fractional distillation of excess cyclohexane from cyclohexanol and cyclohexanone. Such distillation may be effected, for example, at temperatures of 100° to 110° C. The hold-up time in the still is usually sufficient to bring about decomposition of virtually all the hydroperoxide present. The distillation of cyclohexane may take place in more than one stage, and the final removal of cyclohexane may take place by distillation with steam. The cyclohexane so recovered may, of course, be recycled to the oxidation. Decomposition of the hydroperoxide results in the formation of a mixture of cyclohexanol and cyclohexanone, a cobalt compound favouring a higher proportion of cyclohexanol and a chromium compound a higher proportion of cyclohexanone.

After removal of the cyclohexane by distillation the mixed cyclohexanol and cyclohexanone remaining may be recovered by distillation. The still residues which contain high-boiling impurities and the heavy metal compound may be discarded, and may be disposed of, for example by burning.

It has already been proposed to decompose the hydroperoxide in the oxidate obtained in the liquid phase oxidation of cyclohexane with a molecular oxygen-containing gas in the presence of a boron compound by subjecting it to a heat soaking treatment at a temperature of 125° to 200° C., as described, for example, in British Patent Specification No. 1,207,680. The process of our invention may include such a heat soaking treatment, carried out, for example, prior to the hydrolysis of the boric esters. The process of our invention using a said heavy metal compound to decompose the cyclohexylhydroperoxide increases the yield of cyclohexanol and cyclohexanone based on the hydroperoxide present in the oxidate and also based on the cyclohexane converted. Moreover, the process of our invention gives a mixed cyclohexanol and cyclohexanone in which the proportion of monobasic acid impurity, especially of caproic acid is reduced. At a given temperature decomposition of the hydroperoxide with a heavy metal compound is many times faster, e.g. 25 times faster, than thermal decomposition, so that decomposition may generally be effected at lower temperatures.

The invention is illustrated but not limited by the following Examples.

EXAMPLE 1

An oxidate obtained by oxidising cyclohexane with air at 165° C. in the presence of metaboric acid to 5% conversion, after flashing off a part of the cyclohexane, treatment with water to hydrolyse the boric esters of cyclohexanol and separation of water and boric acid, contained 0.82% of cyclohexylhydroperoxide. Chromium octoate, as 0.01% solution in cyclohexane, was added to give levels of 5 and 10 p.p.m. of Cr in the treated oxidate, and the rate of decomposition of the peroxide was measured at 100° and 120° C. in stainless steel tubes treated with phosphate to inhibit decomposition of the peroxide by the metal of the tube itself. The results, expressed as the half-life of the peroxide, are given in the following Table.

TABLE

| Level of Catalyst p.p.m. | Temperature °C. | Peroxide Half-life (minutes) |
|---|---|---|
| 10 | 120 | 1.5 |
| 5 | 120 | 5 |
| 10 | 100 | 5 |
| 5 | 100 | 8-10 |

EXAMPLE 2

An oxidate obtained by oxidising cyclohexane with air at 165° C. in the presence of metaboric acid to 5% conversion was given a heat soaking for 20 min. at 160° C. to 165° C. as described in British Patent Specification No. 1,207,680 and part of the cyclohexane was flashed off. The residue was treated with water to hydrolyse the boric esters of cyclohexanol, and the boric acid and water were separated. The proportion of cyclohexylhydroperoxide in the organic portion was measured. Chromium octoate in cyclohexane, at a level of 5 p.p.m. by weight calculated on the total weight of the organic portion, was added to the organic portion which was then distilled at 100° to 110° C. to remove cyclohexane. The crude mixture of cyclohexanol and cyclohexanone obtained was analysed for purity (the amount oxidisable to adipic acid expressed as a % of the theoretical), caproic acid and cyclohexylhydroperoxide. The crude mixture was subjected to a standard distillation procedure and the yield of distilled product, calculated on cyclohexane converted, was assessed. The yield of the distilled mixture attributable to the cyclohexylhydroperoxide in the organic portion after hydrolysis was 90% of the theoretical. Other results are given in the following Table 2.

EXAMPLE 3 AND COMPARATIVE EXAMPLE 1

Example 3 was a repetition of Example 2 except that the heat-soaking treatment was omitted. In Comparative Example 1, Example 2 was repeated except that the addition of the chromium compound was omitted. In this case the yield of distilled cyclohexanol and cyclohexanone attributable to the cyclohexylhydroperoxide in the organic portion after hydrolysis was 85% of the theoretical. Other results are given in the following Table 2.

TABLE 2

| | Cyclohexanol/Cyclohexanone | | |
|---|---|---|---|
| | Ex. 2 | Ex. 3 | Comparative Ex. 1 |
| Yield of distilled product % by weight (1) | 86.8 | 86.1 | 85.7 |
| Purity of crude product % by weight, as defined | 96.8 | 95.9 | 93.7 |
| Caproic acid content of crude, % by weight | 0.61 | 0.46 | 0.68 |
| Cyclohexylhydroperoxide, after hydrolysis (2) % by weight | 7.0 | 13.0 | 8.0 |
| Cyclohexylhydroperoxide content of crude % by weight | 1.19 | 1.51 | 5.1 |

(1) calculated on cyclohexane converted
(2) calculated on cyclohexane-free organic portion

I claim:

1. A process for the manufacture of cyclohexanol and cyclohexanone which comprises oxidising cyclohexane in the liquid phase with a molecular oxygen-containing gas in the presence of a boron compound with partial conversion of cyclohexane to give an oxidate comprising cyclohexane, boric esters of cyclohexanol and cyclohexylhydroperoxide, treating the said oxidate with water to hydrolyse the said boric esters to cyclohexanol and boric acids, separating the water and boric acids and treating the organic residue with a cyclohexane-soluble peroxide-decomposing heavy metal compound to decompose the cyclohexylhydroperoxide, and separating cyclohexane from the resulting cyclohexanol and cyclohexanone.

2. The process of claim 1 in which the heavy metal compound is a chromium compound.

3. The process of claim 1 in which the heavy metal compound is a cobalt compound.

4. The process of claim 1 in which the heavy metal compound is a salt of an aliphatic or cycloaliphatic carboxylic acid having from 5 to 12 carbon atoms.

5. The process of claim 1 in which the heavy metal compound is added to the organic residue as a solution in a hydrocarbon.

6. The process of claim 1 in which the heavy metal compound is used in the amount of 0.5 to 50 parts per million by weight calculated as metal and expressed on the total weight of the organic residue.

7. The process of claim 1 in which the treatment with the heavy metal compound is effected at a temperature in the range of 70° to 200° C.

8. The process of claim 1 in which the treatment with the heavy metal compound is carried out as a separate step.

9. The process of claim 1 in which the treatment with the heavy metal compound is combined with the removal of at least some of the remaining cyclohexane by distillation.

10. The process of claim 1 which includes a heat-soaking treatment at a temperature of 125° to 200° C.

* * * * *